(12) United States Patent
Meyer et al.

(10) Patent No.: US 8,233,961 B2
(45) Date of Patent: Jul. 31, 2012

(54) MAGNETIC RESONANCE DEVICE AND METHOD FOR PERFUSION DETERMINATION

(75) Inventors: Heiko Meyer, Uttenreuth (DE); Josef Pfeuffer, Newton, MA (US)

(73) Assignee: Siemens Aktiengesellschaft, Munich (DE)

( * ) Notice: Subject to any disclaimer, the term of this patent is extended or adjusted under 35 U.S.C. 154(b) by 1021 days.

(21) Appl. No.: 12/143,265

(22) Filed: Jun. 20, 2008

(65) Prior Publication Data

US 2008/0319302 A1 Dec. 25, 2008

(30) Foreign Application Priority Data

Jun. 22, 2007 (DE) .................. 10 2007 028 901

(51) Int. Cl.
*A61B 5/055* (2006.01)
*G01V 3/00* (2006.01)
(52) U.S. Cl. ......... 600/419; 600/410; 324/307; 324/309
(58) Field of Classification Search .................. None
See application file for complete search history.

(56) References Cited

U.S. PATENT DOCUMENTS

| | | | | |
|---|---|---|---|---|
| 6,564,080 B1 * | 5/2003 | Kimura | ................ | 600/410 |
| 6,717,405 B2 * | 4/2004 | Alsop | ................ | 324/306 |
| 6,980,845 B1 * | 12/2005 | Alsop | ................ | 600/410 |
| 7,328,054 B2 * | 2/2008 | Jesmanowicz | ................ | 600/410 |
| 7,369,888 B2 * | 5/2008 | Alsop | ................ | 600/419 |
| 7,545,141 B2 * | 6/2009 | Kimura | ................ | 324/306 |
| 7,545,142 B2 * | 6/2009 | Alsop | ................ | 324/306 |
| 7,587,233 B2 * | 9/2009 | Wong et al. | ................ | 600/419 |
| 7,627,360 B2 * | 12/2009 | Kimura | ................ | 600/419 |
| 7,865,228 B2 * | 1/2011 | Alsop | ................ | 600/419 |
| 2004/0101048 A1 * | 5/2004 | Paris | ................ | 375/240.12 |
| 2004/0162483 A1 * | 8/2004 | Kimura | ................ | 600/419 |
| 2004/0204643 A1 * | 10/2004 | Jesmanowicz | ................ | 600/410 |
| 2005/0001614 A1 * | 1/2005 | Alsop | ................ | 324/306 |
| 2005/0277828 A1 * | 12/2005 | Alsop | ................ | 600/419 |
| 2007/0132452 A1 * | 6/2007 | Alsop | ................ | 324/306 |
| 2008/0208033 A1 * | 8/2008 | Alsop | ................ | 600/411 |
| 2008/0269595 A1 * | 10/2008 | Wong | ................ | 600/411 |
| 2009/0149733 A1 * | 6/2009 | Guenther | ................ | 600/410 |
| 2009/0253982 A1 * | 10/2009 | Wang | ................ | 600/419 |

(Continued)

FOREIGN PATENT DOCUMENTS

DE 10 2004 043 809 A1 3/2006

(Continued)

OTHER PUBLICATIONS

Liu et al. "Analysis and Design of Perfusion-Based Event-Related fMRI Experiments." NeuroImage, vol. 16, pp. 269-282, 2002.*

(Continued)

*Primary Examiner* — Long V. Le
*Assistant Examiner* — Angela M Hoffa
(74) *Attorney, Agent, or Firm* — Schiff Hardin LLP

(57) ABSTRACT

In a method and a device for automatic determination of perfusion by using a magnetic resonance system, multiple first MR data sets are thereby acquired from a volume element over time with a perfusion-sensitive imaging sequence, and multiple second MR data sets of the same volume element are acquired over time with a control imaging sequence, in particular a perfusion-insensitive imaging sequence. These first MR data sets and the second MR data sets are subjected to a statistical time series analysis in order to determine the perfusion in the volume element.

28 Claims, 2 Drawing Sheets

U.S. PATENT DOCUMENTS

2010/0240983 A1* 9/2010 Jung et al. ............... 600/410
2010/0274117 A1* 10/2010 Gunther et al. ............ 600/410

FOREIGN PATENT DOCUMENTS

EP 2189112 A1 * 5/2010
WO WO 2004/114213 A2 12/2004

OTHER PUBLICATIONS

Hernandez-Garcia et al. "Quantitative Analysis of Arterial Spin Labeling fMRI Data using a General Linear Model." Magnetic Resonance Imaging, vol. 28, pp. 919-927, 2010.*

"Perfusion Functional MRI Reveals Cerebral Blood Flow Pattern under Psychological Stress," Wang et al. Proc. Nat. Acad. Sci., vol. 102, No. 49 (2005) pp. 17804-17809.

"Modeling and Inference of Multisubject fMRI Data," Mumford et al., IEEE Eng. Med. Biol. Magazine, vol. 25 (2005), pp. 42-51.

"Integrating VBM into the General Linear Model with Voxelwise Anatomical Covariates," Oakes et al., NeuroImage, vol. 34 (2007) pp. 500-508.

"Complex Data Analysis in High-Resolution SSFP fMRI," Lee et al., Magnetic Resonance in Medicine, vol. 57 (2007) pp. 905-917.

* cited by examiner

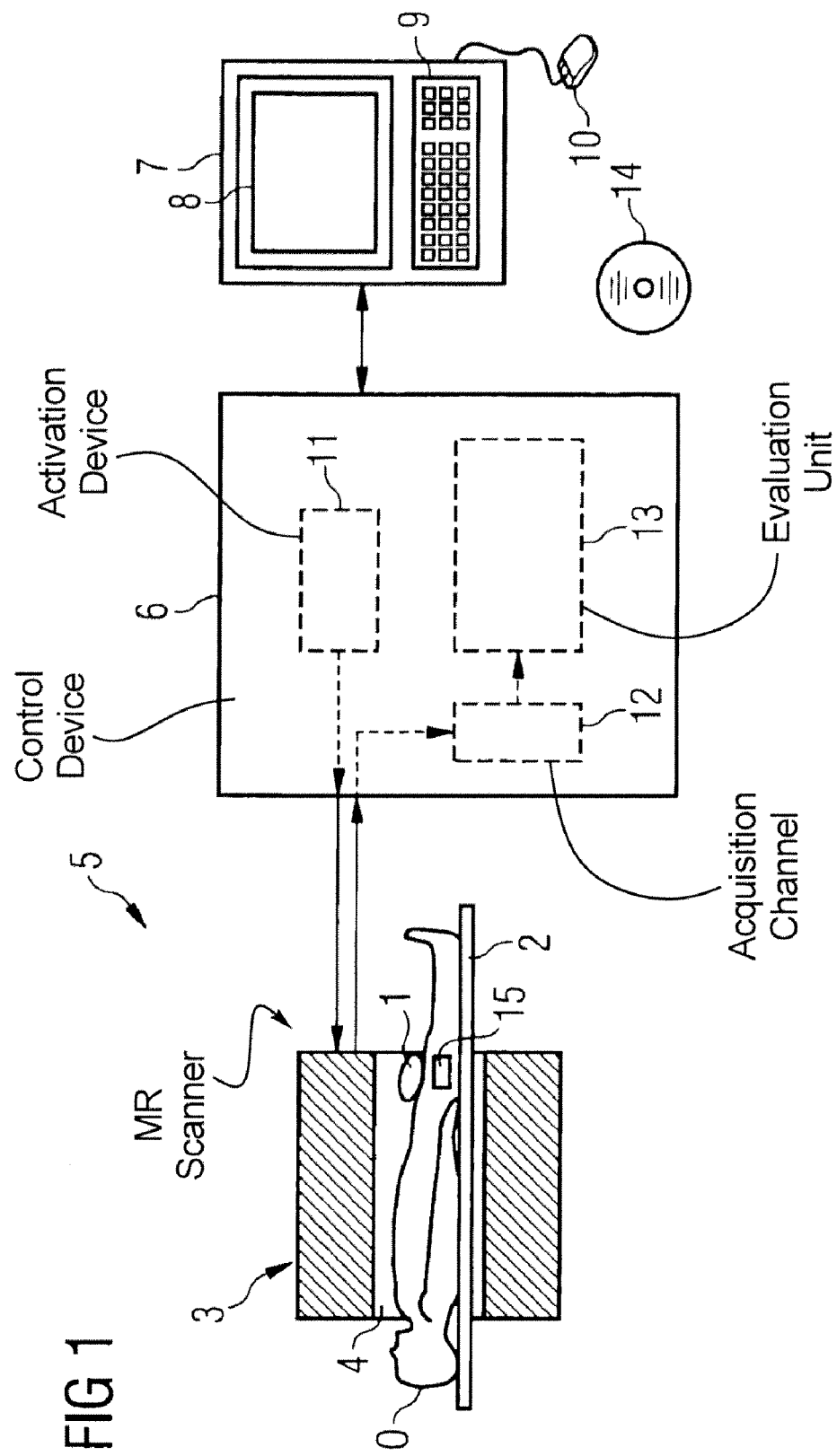

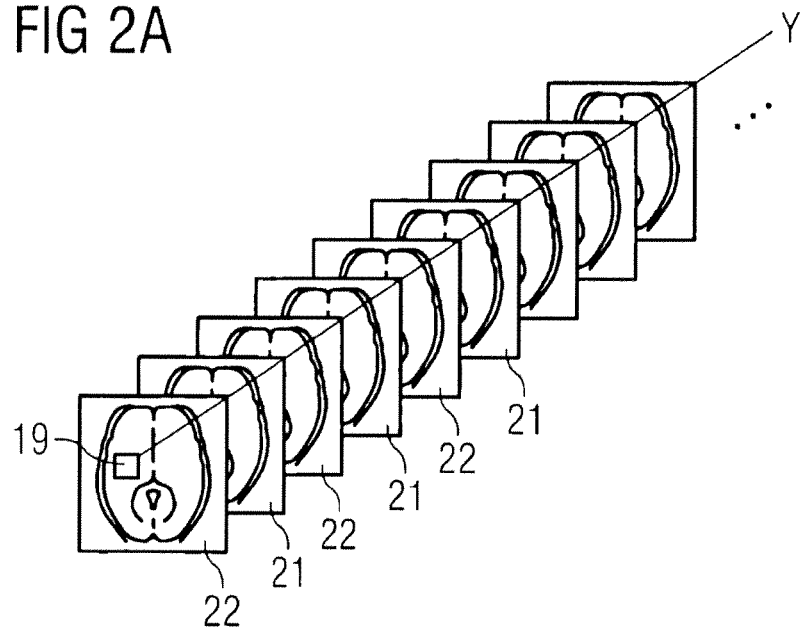

MAGNETIC RESONANCE DEVICE AND METHOD FOR PERFUSION DETERMINATION

BACKGROUND OF THE INVENTION

1. Field of the Invention

The present invention concerns a method and a device in order to automatically determine a perfusion with a magnetic resonance system. Moreover, the present invention concerns a magnetic resonance system designed with the inventive device as well as an electronically readable data medium encoded with programming instructions that cause the method to be executed by a computer.

2. Description of the Prior Art

MR perfusion methods (methods to determine perfusion by means of a magnetic resonance system) are used, for example, in order to measure a blood flow in various body regions, for example in the head (cerebral blood flow (CBF)). CBF is the volume of arterial blood (mL) which flows in 100 g of tissue per minute; in humans a typical value for CBF in the brain is $$\frac{60 \text{ mL}}{100 \text{ g} \times \text{min}}.$$

If the density of the brain is set near to 1 g/mL, CBF in humans is 0.6

$$\frac{\text{mL}}{\text{mL} \times \text{min}} \text{ or } 0.01 \text{ s}^{-1}.$$

With reference to a volume, the dimensions of the CBF are simply the reciprocal of the time, i.e. a rate constant that defines the supply of a tissue volume with arterial blood. CBF has no causal connection with the quantity of the blood within a volume (blood velocity). According to the prior art, ASL methods ("Arterial Spin Labeling" methods) are used during a determination of the perfusion by means of a magnetic resonance system, wherein the water contained in blood is shifted into a particular magnetic state (normally an inverted magnetization); in short: the blood is "labeled" in order to be able to differentiate these blood particles which flow into a considered volume element from other tissue in this volume element. MR images are thereby generated with a perfusion-sensitive image sequence, and MR control images are generated with a control imaging sequence. The perfusion information is thereby represented only by a slight alteration in an image contrast which is present between the labeled blood particles flowing into a region of interest (which labeled blood particles exhibit the particular magnetic state) and the tissue in this region from which the MR images are acquired. A perfusion signal typically exhibits an intensity in the range of only a few percent of the entire intensity of the corresponding MR image. The acquisition of images of a relative perfusion or of images for calculation of a quantitative perfusion is therefore prone to artifacts. For this reason, at present multiple MR images for acquisition of a slight perfusion signal must be generated over multiple minutes, from which a series of MR images characterized with perfusion information and control images (without perfusion information) result over time. An image with perfusion information and a corresponding control image are respectively generated in alternation.

In order to generate MR images in which the perfusion is shown from these images with perfusion information and the corresponding control images, according to the prior art the difference is taken between an image embodying perfusion information and its corresponding control image. The difference value thereby obtained is then averaged over the series of images. A scaling or calibration factor is determined in order to arrive at a relative or quantitative perfusion information in the resulting MR images.

The quality of the conventionally calculated MR images shown perfusion information is low since the methods for determination of perfusion according to the prior art are very error-prone, for example with regard to artifacts or other interferences.

SUMMARY OF THE INVENTION

An object of the present invention is to improve the quality of the MR images depicting perfusion information.

The object is achieved In accordance with the present invention by a method for automatic determination of perfusion with the use of a magnetic resonance system, wherein multiple first MR data sets are generated in succession which are determined with a perfusion-sensitive imaging sequence of a volume element in a body of an organism. Multiple second MR data sets are determined in succession from the same volume element in a similar manner with a control imaging sequence, in particular with a perfusion-insensitive imaging sequence. The first MR data sets and the second MR data sets are evaluated by means of a statistical analysis in order to determine the perfusion in the volume element.

As used herein, a perfusion-sensitive imaging sequence means that particles subject to a perfusion are shifted into a first magnetic state such that these particles, when they flow into the volume element, differ from other particles (for example from the tissue not subject to a perfusion) upon acquisition of the first MR data by the magnetic resonance system. The particles subjected to the perfusion are shifted into a second magnetic state by the control imaging sequence, this second magnetic state being easy to differentiate from the first magnetic state in the determination of the second MR data by the magnetic resonance system, and being advantageously insensitive to perfusion effects.

In contrast to the prior art, in the method according to the invention no difference is taken between the first MR data sets and the second MR data sets in order to determine the perfusion; rather, the entirety of the first MR data sets and second MR data sets is subjected to a statistical analysis. Because, according to the invention, no difference is taken between the first MR data and the second MR data, a corresponding absolute value can advantageously also be calculated from the first MR data and the second MR data sets, and this absolute value can be used to determine the perfusion.

In the method according to the invention, a sequence of MR images is generated in particular starting from the first MR data sets and the second MR data sets, and a signal curve is determined for individual, respectively corresponding image points or voxels within these MR images. This signal curve is then advantageously evaluated by means of statistical analysis. The statistical analysis determines coefficients which are then analyzed in order to determine information about the perfusion.

In a preferred exemplary embodiment, a first MR data set followed by second MR data set followed again by first MR data set, etc. are acquired in alternation for the volume element. In other words, an MR image is generated by the magnetic resonance system with the perfusion-insensitive imaging sequence and an MR image with the control imaging sequence, are respectively generated in alternation. The signal curve of a voxel exhibiting a perfusion relative to a perfusion-sensitive value detected by the magnetic resonance system then exhibits a zigzag shape since the value in the first MR data set exhibits a high measurement value, for example, and correspondingly exhibits a comparatively low measurement value in the second MR data set. This zigzag signal curve can then be evaluated with statistical analysis in order to determine the perfusion information for the corresponding voxel.

The statistical analysis can be conducted according to the General Linear Model or according to the Student's t-Test. Other statistical methods such as, for example, a cross-correlation can alternatively be used.

A relative perfusion information or even a quantitative perfusion information can thereby be determined with the General Linear Model while the Student's t-Test is in particular used in order to draw a conclusion of whether the intensity of an image element in the first MR data set differs from the intensity of a corresponding image point in the second MR data set. Moreover, conclusions can be drawn about the quality of the first and second MR data which can then advantageously be used in order to exclude specific first and/or second MR data from the determination of the perfusion information (for example due to poor quality) and/or to assign an operator to acquire additional first and second MR data since sufficient first and second MR data of a satisfactory quality are not yet present.

Statistical measured values of a contrast within inventively generated MR images which correlate directly with a contrast-to-noise ratio with regard to the perfusion information in the MR images can specifically be calculated with the Student's t-Test. A display of these measured values or of the contrast-to-noise ratio occurring in real time enables an operator to track a quality of the perfusion information within the inventively generated MR images dependent on the time in which the first and second MR data are acquired.

To improve the perfusion information by statistical analysis, at least one model function or a function modality can be added to the statistical analysis as at least one regressor. The at least one regressor corresponds to one or more regressor from a group that includes the following regressors:
  Regressors that are derived from measurement results acquired by the magnetic resonance system. For example, if systematic errors of the magnetic resonance system can be deduced from the measurement results, these errors can be taken into account by the statistical analysis via a corresponding model function. Movements of an organism for which the determination of the perfusion is implemented can be detected via the measurement results as long as movements are of a rigid body (thus no deformation of the body occurs in the movement).
  Regressors that are detected by devices not belonging to the magnetic resonance system. If interferences which influence the acquisition of the first and second MR data are detected by these devices, these interferences can be taken into account by the statistical analysis by a corresponding model function.
  Regressors that are derived from functional changes or variations of the organism. The "functional change" is in particular a change of a physiological state of the organism or a functional activity of the organism. An example of a functional activity is a periodic movement of a body part (for example a finger) of the organism. The functional activity can thereby be detected via variations of the perfusion, via variations of a cerebral blood flow or via variations in the BOLD ("Blood Oxygenation Level Dependent") effect.

By a regressor, what is thereby understood (corresponding to the statistical analysis) is an explanatory variable which exhibits an explanatory influence on a variable to be explained (in particular on the perfusion in the present invention). There are unwanted or interfering regressors such as, for example, unplanned movements of the organism, but also desired or, respectively, useful regressors such as, for example, a planned functional activity of the organism. Although both unwanted and desired regressors can be taken into account by the statistical analysis in the determination of the perfusion according to the invention, the desired regressors can be planned better or more precisely in the General Linear Model, for example, since it known beforehand that the corresponding regressor exists and when it occurs.

These model functions, together with a perfusion model with which a conclusion can be drawn about the perfusion, form an input for a multi-dimensional statistical analysis according to the General Linear Model.

According to the invention, the group of regressors can also include the following regressors:
  A movement of the organism. This means an unplanned movement.
  A scanning stability of the magnetic resonance system. The acquisition of the first and second MR data sometimes undergoes certain fluctuations if a stability with which the magnetic resonance system acquires the first and second MR data is not constant.
  A breathing of the organism. At least one part of the organism moves dependent on the breathing.
  A heart beat of the organism. At least the heart of the organism moves dependent on the heart beat, and on the other hand a flow speed of the blood also depends on the heart beat, for example.

The method according to the invention is not only able to generate perfusion information, but also can determine the following additional results:
  Information about a reliability of results determined by the inventive method for the corresponding volume element. For example, a quality declaration of how good specific quantitative information determined according to the invention (for example) can be made by means of the Student's t-Test.
  Information about a contrast-to-noise ratio for a specific image point within the volume element. A conclusion about the quality of the perfusion information determined by the method according to the invention is thereby advantageously possible.
  Information about the following artifacts:
    a breathing of the organism
    a heart beat of the organism
    a movement of the organism
    a functional activity of the organism
    the BOLD effect.

The information about the artifacts thereby comprise a conclusion about the scope or the extent of the artifacts, for example, which in turn allows a conclusion of the quality of the determined perfusion information. For example, if it is detected through the statistical analysis that the breathing and/or the movement of the organism was disproportionately severe in the acquisition of the first and second MR data, such that the quality of the perfusion information could thereby be affected, this information can be valuable for an evaluation of the perfusion information.

According to the invention, images (maps) can also be generated that represent an intensity and/or statistical significance of the various regressors separated per regressor. Which voxels within a specific MR image are influenced by the breathing, the heart beat, a movement, etc. can be derived via this images, for example.

A quality control of the acquired first and second MR data sets can be effected with the aid of the results described in the preceding. For example, depending on the results, already generated first and/or second MR data sets can additionally be excluded from the method, i.e., they are not analyzed. Moreover, further first and/or second MR data can be generated if the results suggest this. For example, this can be the case when the statistical analysis detects that a scope or an extent of one or more artifacts lies above a predetermined threshold. The quality of the detected first and second MR data sets is strongly influenced by a too-severe movement of the organism that is too severe, for example, wherein this movement itself is detected in the evaluation of the MR data. A false positive or a false negative perfusion information can also be derived from the results described above and be used for quality control.

With the method according to the invention, MR images which contain the following information can also be generated through the statistical analysis:
- A change of the blood oxygenation of a tissue of the considered volume element. Since the BOLD effect has an effect on the results acquired by a magnetic resonance system, the change of the blood oxygenation can be derived from the first and second MR data.
- A functional activity of the organism. Since the functional activity of the organism likewise exhibits an effect on the results acquired by the magnetic resonance system, a scope of a functional activity can also be derived from the first and second MR data.
- A result of a correlation between the BOLD effect and a specific functional activity. Since the statistical analysis is already used to determine the perfusion information, it is advantageously no great additional effort to also determine the correlation between the BOLD effect and a specific functional activity.

According to the invention, MR images that contain the perfusion information and are generated starting from the first and second MR data can be continuously generated in real time so that they are continuously updated with new first and second MR data acquired according to the invention. In other words, a first series of MR images which represent the perfusion information is in particular generated when the statistical analysis has determined in advance that the perfusion information shown in this first series possesses a corresponding quality. This first series is then updated continuously starting from the already determined first and second MR data and further newly acquired first and second MR data.

The first and second MR data sets can naturally also be first evaluated after the conclusion of the acquisition of all first and second MR data sets.

The MR images generated by the method according to the invention and which exhibit the perfusion information can be generated either starting from the entirety of the first and second MR data which were acquired according to the invention or can be generated starting from a specific sub-set of the first and second MR data sets. If the MR images are generated from a sub-set of the first and second MR data sets, this sub-set in particular contains no first and second MR data sets, which are unusable according to the statistical analysis for determination of the perfusion information. Moreover, this sub-set comprises as up-to-date as possible first and second MR data sets, such that the oldest first and second MR data sets can be periodically removed from this sub-set, for example.

If the statistical analysis is executed with the General Linear Model, coefficients of this General Linear Model can be scaled such that a declaration about a relative perfusion and/or a declaration about an absolute perfusion can be made with these coefficients.

The present invention also encompasses a device for a magnetic resonance system for automatic determination of perfusion. This device has a control unit to control the magnetic resonance system, a receiver device to receive multiple first and second MR data sets which are acquired by the magnetic resonance system (in particular by local coils), and an evaluation device in order to evaluate these first and second MR data sets and to generate MR images therefrom. The device is designed such that it controls the magnetic resonance system to cause the magnetic resonance system to acquire or record the first and second MR data sets. The control device controls the magnetic resonance system such that the magnetic resonance system effects a perfusion-sensitive imaging sequence with regard to the volume element for the acquisition of the first MR data sets and effects a control imaging sequence, in particular a perfusion-insensitive imaging sequence with regard to the volume element, for the acquisition of the second MR data set. The device is able to conduct a statistical analysis of the first and second MR data sets with the aid of its evaluation device in order to determine the perfusion in the volume element.

The advantages of the device according to the invention significantly corresponding to the advantages of the method according to the invention.

The present invention also encompasses a magnetic resonance system that embodies the device described above.

The present invention also encompasses an electronically readable data medium (for example a DVD) on which is stored electronically-readable control information (in particular programming instructions). All embodiments of the method described above can be implemented when this control information is read from the data medium and stored in a controller of a magnetic resonance system.

The acquisition and the evaluation of MR images that contain perfusion information are significantly improved with the present invention compared to the prior art. According to the invention, information about the precision of the determined results (for example quantitative perfusion information), about a contrast-to-noise ratio and about a scope of specific artifacts can also be determined in addition to perfusion information. This information can be presented in the form of images.

The present invention is in particular suitable for a determination of perfusion or flows of liquids in the body of an organism by means of a magnetic resonance system in order to make the perfusion visible in MR images. Naturally, the present invention is not limited to this preferred application field; rather it can also be used in order to determine further information or results such as, for example, a change of the blood oxygenation of a tissue, an extent of a functional activity or the quality of information presented in an MR image. In general the method according to the invention can be used when information is to be determined from data sets which contain this information and from control data sets which primarily differ from the data sets in that they do not exhibit information.

BRIEF DESCRIPTION OF THE DRAWINGS

FIG. 1 shows a magnetic resonance system according to the invention with a device according to the invention.

FIG. 2A shows a time series of first and second MR data sets or MR images, obtained in accordance with the invention.

FIG. 2B shows a corresponding General Linear Model of the first and second MR data sets.

DESCRIPTION OF THE PREFERRED EMBODIMENTS

FIG. 1 shows an exemplary embodiment for a magnetic resonance system 5 with which an automatic determination of perfusion is possible. The core of this magnetic resonance system 5 is a scanner (MR data acquisition unit) 3 in which is positioned a patient O on a recumbent board 2 in an annular basic field magnet (not shown) which surrounds a measurement volume 4.

The recumbent board 2 can be displaced in the longitudinal direction, i.e. along the longitudinal axis of the scanner 3. A whole-body coil (not shown), with which radio-frequency pulses can be emitted and also received is located within the basic field magnet in the scanner 3. Moreover, the scanner 3 contains gradient coils (not shown) in order to be able to apply a magnetic field gradient in each of the three spatial directions.

The scanner 3 is controlled by a control device 6 which here is shown separate from the scanner 3. A terminal 7 that includes a screen 8, a keyboard 9 and a mouse 10 is connected to the control device 6. The terminal 7 in particular serves as a user interface via which an operator operates the control device 6 and therefore the scanner 3. Both the control device 6 and the terminal 7 are components of the magnetic resonance system 5.

Moreover, a DVD 14 is shown in FIG. 1 on which software is stored with which the method according to the invention can be executed when the software has been loaded into the control device 6.

Furthermore, the magnetic resonance system 5 has all further typical components or features such as, for example, interfaces for connection of a communication network (for example of an image information system) or the like. All of these components are not shown in FIG. 1 for better clarity.

An operator can communicate with the control device 6 via the terminal 7 and thus provide for an implementation of desired measurements in that, for example, the scanner 3 is controlled by the control device 6 such that required radio-frequency pulse sequences are emitted by the antenna and the gradient coils are switched in a suitable manner. First MR data sets 21 and second MR data sets 22 from the scanner 3 are also acquired by the control device 9 and converted into corresponding images (MR images) in an evaluation unit 13 (which is a module of the control device 6). These images are then shown on the screen 8 and/or stored in a memory or sent over a network, for example.

The recumbent board 2 can be moved by motors within the scanner 3 by means of the control device 6. The control device 6 has an activation unit 11 that automatically moves the recumbent board 2 through scanner 3 so that it occupies various positions within the scanner 3. Moreover, the activation device 11 ensures that a defined magnetic field gradient is applied a radio-frequency shield which essentially corresponds to the magnetic resonance frequency is simultaneously emitted by the whole-body coil. Alternatively, the radio-frequency signal can be emitted with a specially designed local coil (transmission/reception coil).

The first MR data set 21 and the second MR data set 22 from a corresponding volume element 15 in the body of the patient O are then determined and acquired with a local coil 1 with the aid of an acquisition channel 12, or a measurement device of the control device 6. MR images in which a perfusion is shown are generated in the evaluation device 13 from these first MR data set or MR images 21 and second MR data set or MR images 22.

A time series of first MR images 21 and second MR images 22 is shown in FIG. 2a. Arterial blood within a head of the organism O which flows in a considered voxel 19 was thereby labeled by means of ASL ("Arterial Spin Labeling") in the acquisition of the first MR images 21, such that blood flowing into the voxel is differentiable from the tissue within the volume element. In contrast to this, no such labeling of the arterial blood occurs in the acquisition of the second MR images. As shown in FIG. 2A, a second MR image 22 is respectively acquired after an acquisition of a first MR image 21, and a first MR image 21 is acquired after each second MR image 22. In other words: the series of first and second MR images 21, 22 acquired over time alternates: first MR image 21, second MR image 22, etc.

The white rectangle labeled with the reference character 19 corresponds to the voxel in which the perfusion is currently determined. It s noted that the volume element 15 in FIG. 1 is shown within a leg of the patient I while the voxel 19 in FIG. 2A is arranged within the head of the patient.

The General Linear Model is shown in FIG. 2B. Individual component values of the left vector Y ($y_1$, $y_2$, $y_3$, etc.) thereby correspond to individual measurement values with regard to the voxel 19 of correspondingly many first and second MR images 21, 22 in chronological order. In other words: the vector Y corresponds to a signal curve over time of an image point or voxel 19 of successive MR images 21, 22.

The matrix standing directly to the right of the equals sign contains a perfusion model 18 on the one hand and three function models 17 on the other hand. The perfusion model 18 is thereby a vector which possesses the values 1, 0, 1, 0, etc., such that a grey line corresponds to a 1 and a white line corresponds to a 0 in FIG. 2B. A value of 1 thereby means that the corresponding component of the Y-vector contains perfusion information and the value 0 states that the corresponding component of the Y-vector contains no perfusion information.

The three function models 17 are a function model to depict a stability or, respectively, instability of a scanning behavior of the acquisition device 12. A function model to depict the heart beat of the patient O and a function model to depict a functional activity (such as, for example, a periodic movement of a finger of the patient O) can likewise be used here. The vectors 17 representing a corresponding function model thereby normally respectively exhibit a 1 as a component value when the instability exists or, respectively, the heart beats just then, or the finger is moved or a 0 when this is not the case. For example, if the BOLD effect exhibits an increased value for some time during the acquisition of the first and second MR images 21, 22, a corresponding vector (not shown) of a function model representing the BOLD effect would have a 1 as a component value in this time period both for the corresponding first MR images 21 and for the corresponding second MR images 22.

The matrix composed of the perfusion model 18 and the three function models 17 is also designated as a design matrix.

It is noted that a component value −1 can also be used instead of a component value of 0 in the General Linear Model, such that the vectors of the design matrix 17, 18 then exhibit the component values −1 and +1.

The vector with which the design matrix 17, 18 is multiplied contains coefficients $\mu$, $T_1$, $T_2$, $T_3$ or, respectively, quantitative parameters to be determined by the statistical analysis with the General Linear Model 16. The parameter $\mu$ indicates a quantitative value for the perfusion in the voxel 19. In the same manner the parameter $\tau_1$ indicates a quantitative value for the stability of the scanning behavior of the acquisition device 12, the parameter $\tau_2$ of a quantitative value for the heart beat of the patient O and the parameter $\tau_3$ indicates a quantitative value for the functional activity of the patient O with regard to the voxel 19.

A vector U ($u_1$, $u_2$, $u_3$, ... ) contains (represents) remainder errors which are caused by noise or are formed by errors that are not depicted by the function model 17.

The determination of the perfusion or, respectively, of the parameter $\Xi$ as well as of the parameters $\tau_1$, $\tau_2$, $\tau_3$ thereby ensues by means of the General Linear Model adapted due to the design of the design matrix 17, 18, starting from the corresponding measurement values for different voxels, such that ultimately information about the perfusion (and about the stability of the scanning behavior, the heart beat and the functional activity) can be determined and presented in a larger volume segment. The parameter $\mu$ can the be scaled such that it represents a relative or even and absolute perfusion value (unit:

$$\left(\text{unit:}\ \frac{mL}{100\ g \times min}\right).$$

With an appropriate selection of a function model 17, probabilities and other statistical measured values which represent a measured value of the reliability or of the quality of the results (for example perfusion) determined per voxel can also be determined with the General Linear Model by the corresponding coefficients $\tau_1$, $\tau_2$, $\tau_3$.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatic determination of perfusion in a magnetic resonance (MR) system, comprising the steps of:
    (a) generating multiple first MR data sets from a volume element of a subject over time using a perfusion-sensitive imaging sequence;
    (b) generating multiple second MR data sets of said volume element of said subject over time using a control MR imaging sequence;
    (c) obtaining a statistical analysis result by statistically analyzing said first MR data sets and said second MR data sets with at least one model function embodying at least one regressor, and selecting said at least one regressor from the group consisting of regressors representing breathing of the subject, regressors representing a heartbeat of the subject, regressors representing a physiological state of the subject, and regressors representing functional activity of the subject, and, using said statistical analysis result, determining perfusion in said volume element, as determined perfusion;
    (d) tracking quality of the determined perfusion in said volume element by also statistically analyzing said first MR data sets and said second MR data sets to obtain at least one further result, other than said statistical analysis result from which said perfusion is determined, selected from the group consisting of a reliability indicator for said determination of said perfusion of said volume element, information describing a contrast-to-noise ratio for an image point of said volume element, and information describing at least one characteristic of said subject that may produce an artifact in an image reconstructed from said first MR data sets and said second MR data sets and using said at least one further result to exclude at least a portion of at least one of said first and second MR data sets for which said at least one further result indicates a poor quality, to produce quality-tracked first and second MR data sets; and
    (e) continuously reconstructing MR images of said volume from said quality-tracked first MR data sets and said second MR data sets, and continuously updating said MR images with newly acquired multiple first MR data sets and multiple second MR data sets to which steps (c) and (d) are also applied.

2. A method as claimed in claim 1 comprising employing a perfusion-insensitive MR imaging sequence as said control MR imaging sequence.

3. A method as claimed in claim 2 comprising generating said perfusion-sensitive MR imaging sequence using a perfusion-sensitive magnetic field gradient adjustment, and generating said perfusion-sensitive MR imaging sequence using a perfusion-sensitive magnetic field gradient adjustment.

4. A method as claimed in claim 1 comprising reconstructing a sequence of said MR images from said first MR data sets and said second MR data sets and identifying a signal curve over time of at least one individual image point in said sequence of said MR images, and using said signal curve to produce said signal analysis result.

5. A method as claimed in claim 4 comprising using said signal curve to produce said signal analysis result by identifying coefficients of said signal curve and determining said perfusion in said volume element by analyzing said coefficients.

6. A method as claimed in claim 1 comprising acquiring a portion of said first MR data sets in alternation with a portion of said second MR data sets.

7. A method as claimed in claim 1 comprising statistically analyzing said first MR data sets and said second MR data sets using a statistical analysis procedure selected from the group consisting of the General Linear Model, the Student's t-Test and cross-correlations.

8. A method as claimed in claim 1 comprising statistically analyzing said first MR data sets and second MR data sets with at least one model function embodying at least one further regressor, and selecting said at least one further regressor from the group consisting of regressors derived from measurement results acquired by the magnetic resonance system, regressors that are detected by devices independent of the magnetic resonance system, and regressors derived from functional changes of a subject from which said first MR data sets and said second MR data sets are acquired.

9. A method as claimed in claim 1 comprising selecting said information describing said at least one characteristic from the group consisting of information representing breathing of the subject, information representing a heartbeat of the subject, information representing movement of the subject, information representing functional activity of the subject, and information representing the BOLD effect in the subject.

10. A method as claimed in claim 1 comprising statistically analyzing said first MR data sets and said second MR data sets to obtain, as said at least one further result, said information describing at least one characteristic of said subject that may produce an artifact in an image reconstructed from said first MR data sets and said second MR data sets, by analyzing said first and second MR data sets to determine whether artifacts exist therein and whether said artifacts are above a predetermined threshold and, if so, producing said quality tracked first and second MR data sets by excluding at least a portion of at least one of said first MR data sets and said second MR data sets responsible for said artifacts.

11. A method as claimed in claim 1 comprising reconstructing said MR images so as to contain at least one representation selected from the group consisting of a blood oxygenation content of tissue of the volume element, functional activity of the subject from whom the first MR data sets and the second MR data sets are acquired, and a result of correlation of the BOLD effect with functional activity of the subject from whom the first MR data sets and the second MR datasets are acquired.

12. A method as claimed in claim 1 comprising reconstructing MR images of the volume element from at least a sub-set of said first MR data sets and said second MR data sets.

13. A method as claimed in claim 1 comprising statistically analyzing said first MR data sets and said second MR data sets using the General Linear Model, said General Linear Model embodying coefficients, and scaling said coefficients of said General Linear Model to produce a perfusion unit in said volume element selected from the group consisting of a relative perfusion unit and an absolute perfusion unit.

14. A device for automatic determination of perfusion in a magnetic resonance (MR) system, comprising:
an input configured to receive, from said magnetic resonance system, multiple first MR data sets acquired from a volume element of a subject over time using a perfusion-sensitive imaging sequence and multiple second MR data sets of said volume element of the subject acquired over time using a control MR imaging sequence;
a processor being configured to (a) obtain a statistical analysis result by statistically analyzing said first MR data sets and said second MR data sets with at least one model function embodying at least one regressor, and to select said at least one regressor from the group consisting of regressors representing breathing of the subject, regressors representing a heartbeat of the subject, regressors representing a physiological state of the subject, and regressors representing functional activity of the subject, and, (b) to use said statistical analysis result determining perfusion in said volume element, as determined perfusion;
said processor being configured to (c) track quality of the determined perfusion in said volume element by also statistically analyzing said first MR data sets and said second MR data sets to obtain at least one further result, other than said statistical analysis result from which said perfusion is determined, selected from the group consisting of a reliability indicator for said determination of said perfusion of said volume element, information describing a contrast-to-noise ratio for an image point of said volume element, and information describing at least one characteristic of said subject that may produce an artifact in an image reconstructed from said first MR data sets and said second MR data sets and (d) to use said at least one further result to exclude at least a portion of at least one of said first and second MR data sets for which said at least one further result indicates a poor quality, to produce quality-tracked first and second MR data sets; and
said processor being configured to continuously reconstruct MR images of said volume element from said quality-tracked first MR data sets and said second MR data sets, and to continuously update said MR images with newly acquired multiple first MR data sets and multiple second MR data sets by implementing (a), (b), (c) and (d).

15. A device as claimed in claim 14 wherein said processor is configured to reconstruct a sequence of said MR images from said first MR data sets and said second MR data sets and to identify a signal curve over time of at least one individual image point in said sequence of said MR images, and using said signal curve to produce said signal analysis result.

16. A device as claimed in claim 15 wherein said processor is configured to use said signal curve to produce said signal analysis result by identifying coefficients of said signal curve and to determine said perfusion in said volume element by automatically analyzing said coefficients.

17. A device as claimed in claim 14 wherein said processor is configured to statistically analyze said first MR data sets and said second MR data sets using a statistical analysis procedure selected from the group consisting of the General Linear Model, the Student's t-Test and cross-correlations.

18. A device as claimed in claim 14 wherein said processor is configured to statistically analyze said first MR data sets and second MR data sets with at least one model function embodying at least one further regressor, and to select said at least one further regressor from the group consisting of regressors derived from measurement results acquired by the magnetic resonance system, regressors that are detected by devices independent of the magnetic resonance system, and regressors derived from functional changes of a subject from which said first MR data sets and said second MR data sets are acquired.

19. A device as claimed in claim 14 wherein said processor is configured to employ, as said information describing said at least one characteristic, information selected from the group consisting of information representing breathing of the subject, information representing a heartbeat of the subject, information representing movement of the subject, information representing functional activity of the subject, and information representing the BOLD effect in the subject.

20. A device as claimed in claim 14 wherein said processor is configured to statistically analyze said first MR data sets and said second MR data sets to obtain, as said at least one further result, said information describing at least one characteristic of said subject that may produce an artifact in an image reconstructed from said first MR data sets and said second MR data sets, and by analyzing said first and second MR data sets to determine whether artifacts exist therein and whether said artifacts are above a predetermined threshold and, if so, to produce said quality-tracked first and second MR data sets by excluding at least a portion of at least one of said first MR data sets and said second MR data sets responsible for said artifacts.

21. A device as claimed in claim 14 wherein said processor is configured to reconstruct said MR images so as to contain at least one representation selected from the group consisting of a blood oxygenation content of tissue of the volume element, functional activity of the subject from whom the first MR data sets and the second MR data sets are acquired, and a result of correlation of the BOLD effect with functional activity of the subject from whom the first MR data sets and the second MR datasets are acquired.

22. A device as claimed in claim 14 wherein said processor is configured to reconstruct said MR images of the volume element from at least a sub-set of said first MR data sets and said second MR data sets.

23. A device as claimed in claim 14 wherein said processor is configured to statistically analyze said first MR data sets and said second MR data sets using the General Linear Model, said General Linear Model embodying coefficients, and to scale said coefficients of said General Linear Model to produce a perfusion unit in said volume element selected from the group consisting of a relative perfusion unit and an absolute perfusion unit.

24. A magnetic resonance system (MR) for automatic determination of perfusion in a subject comprising:
  an MR data acquisition unit configured to interact with a subject to acquire multiple first MR data sets from a volume element of the subject over time using a perfusion-sensitive imaging sequence, and to achieve multiple second MR data sets of said volume element over time using a control MR imaging sequence; and
  a processor configured to (a) obtain a statistical analysis result by statistically analyzing said first MR data sets and said second MR data sets with at least one model function embodying at least one regressor, and to select said at least one regressor from the group consisting of regressors representing breathing of the subject, regressors representing a heartbeat of the subject, regressors representing a physiological state of the subject, and regressors representing functional activity of the subject, and, (b) to use said statistical analysis result determining perfusion in said volume element, as determined perfusion, and said processor being configured to (c) track quality of the determined perfusion in said volume element by also statistically analyzing said first MR data sets and said second MR data sets to obtain at least one further result, other than said statistical analysis result from which said perfusion is determined, selected from the group consisting of a reliability indicator for said determination of said perfusion of said volume element, information describing a contrast-to-noise ratio for an image point of said volume element, and information describing at least one characteristic of said subject that may produce an artifact in an image reconstructed from said first MR data sets and said second MR data sets and (d) to use said at least one further result to exclude at least a portion of at least one of said first and second MR data sets for which said at least one further result indicates a poor quality, to produce quality-tracked first and second MR data sets, and said processor being configured to continuously reconstruct MR images of said volume element from said quality-tracked first MR data sets and said second MR data sets, and to continuously update said MR images with newly acquired multiple first MR data sets and multiple second MR data sets by implementing (a), (b), (c) and (d).

25. A system as claimed in claim 24 wherein said MR data acquisition unit is configured to acquire a perfusion-insensitive MR imaging sequence as said control MR imaging sequence.

26. A device as claimed in claim 25 wherein said MR data acquisition unit is configured to acquire said perfusion-sensitive MR imaging sequence using a perfusion-sensitive magnetic field gradient adjustment, and to acquired said perfusion-sensitive MR imaging sequence using a perfusion-sensitive magnetic field gradient adjustment.

27. A device as claimed in claim 24 wherein said MR data acquisition unit is configured to acquire a portion of said first MR data sets in alternation with a portion of said second MR data sets.

28. A non-transitory, computer-readable storage medium encoded with programming instructions for automatic determination of perfusion in a magnetic resonance (MR) system having an MR data acquisition unit and a processor, said programming instructions causing:
  said MR data acquisition unit to generate multiple first MR data sets from a volume element of a subject over time using a perfusion-sensitive imaging sequence, and to generate multiple second MR data sets of said volume element of said subject over time using a control MR imaging sequence;
  said processor to (a) obtain a statistical analysis result by statistically analyzing said first MR data sets and said second MR data sets with at least one model function embodying at least one regressor, and to select said at least one regressor from the group consisting of regressors representing breathing of the subject, regressors representing a heartbeat of the subject, regressors representing a physiological state of the subject, and regressors representing functional activity of the subject, and, (b) to use said statistical analysis result determining perfusion in said volume element, as determined perfusion;
  said processor to (c) track quality of the determined perfusion in said volume element by also statistically analyzing said first MR data sets and said second MR data sets to obtain at least one further result, other than said statistical analysis result from which said perfusion is determined, selected from the group consisting of a reliability indicator for said determination of said perfusion of said volume element, information describing a contrast-to-noise ratio for an image point of said volume element, and information describing at least one characteristic of said subject that may produce an artifact in an image reconstructed from said first MR data sets and said second MR data sets and (d) to use said at least one further result to exclude at least a portion of a least one of said first and second MR data sets for which said at least one further result indicates a poor quality, to produce quality-tracked first and second MR data sets; and
  said processor to continuously reconstruct MR images of said volume element from said quality-tracked first MR data sets and said second MR data sets, and to continuously update said MR images with newly acquired multiple first MR data sets and multiple second MR data sets by implementing (a), (b), (c) and (d).

* * * * *